United States Patent [19]

Sato et al.

[11] Patent Number: 4,560,763

[45] Date of Patent: Dec. 24, 1985

[54] BASE PRECURSOR FOR HEAT-DEVELOPABLE PHOTOSENSITIVE MATERIAL

[75] Inventors: Kozo Sato; Hiroyuki Hirai, both of Kanagawa, Japan

[73] Assignee: Fuji Photo Film Co., Ltd., Kanagawa, Japan

[21] Appl. No.: 595,121

[22] Filed: Mar. 30, 1984

[30] Foreign Application Priority Data

Mar. 31, 1983 [JP] Japan .................................. 58-55700

[51] Int. Cl.$^4$ .................... C07D 213/55; C07C 69/52; C07C 69/76; G03C 5/24; G03C 1/00
[52] U.S. Cl. .................................. 546/341; 562/598; 562/493; 562/480; 562/510; 562/490; 562/405; 546/174; 549/79; 548/146; 548/217; 548/499; 548/494; 548/332; 548/330; 430/151; 430/619
[58] Field of Search ............... 562/598, 493, 480, 510, 562/490, 405; 546/341, 174; 549/79; 548/146, 217, 499, 494, 342, 330; 430/151, 619

Primary Examiner—Paul R. Michl
Assistant Examiner—Alex H. Walker
Attorney, Agent, or Firm—Sughrue, Mion, Zinn, Macpeak & Seas

[57] ABSTRACT

A base precursor for heat-developable photosensitive material is disclosed. The precursor is comprised of a compound represented by general formula (I) or (II):

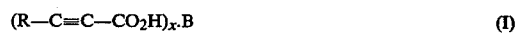

$$(R-C{\equiv}C-CO_2H)_x \cdot B \qquad (I)$$

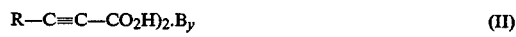

$$R-C{\equiv}C-CO_2H)_2 \cdot B_y \qquad (II)$$

The substituents within the general formulae are defined within the specification. The use of this novel base precursor makes it possible to obtain a material which is very stable at normal temperatures and which smoothly decomposes under heating at 80° C. or higher in order to release a basic constituent.

5 Claims, No Drawings

BASE PRECURSOR FOR HEAT-DEVELOPABLE PHOTOSENSITIVE MATERIAL

FIELD OF THE INVENTION

The present invention relates to a novel base precursor for heat-developable photosensitive material. The term "base percursor" here means one which thermally decomposes by heating to release a basic constituent. In heat-developable photosensitive material, it is desirable to employ bases in order to accelerate the development with heat and it is necessary to use the bases as precursor form for enhancing the stability of photosensitive material. In order to make practical use of these base presursors, they must be stabilized at room temperature and their decomposition during heating must be made smooth.

BACKGROUND OF THE INVENTION

Examples of conventional base precursors include ureas as described in U.S. Pat. No. 2,732,299 and Belgian Pat. No. 625,554, a urea or an ammonium salt of urea with weak acid as described in Japanese Patent Publication No. 1699/65, hexamethylenetetramines and semicarbazides as described in U.S. Pat. No. 3,157,503, triazine compounds and carboxylic acids as described in U.S. Pat. No. 3,493,374, dicyandiamide derivatives as described in U.S. Pat. No. 3,271,155, N-sulfonylureas as decribed in U.S. Pat. No. 3,420,665, amineimides as described in *Research Disclosure*, No. 15776 (1977), and thermo-degradative acid salts represented by trichloroacetic acid as described in British Pat. No. 998,949.

However, an image forming material using these base precursors has essentially serious defects. Specifically, a high image density cannot be obtained or the S/N ratio of the image is considerably decreased due to the release of base during preservation. This takes place because they do not possess good stability at normal temperature and do not smoothly decompose during the developing process.

SUMMARY OF THE INVENTION

A primary object of the present invention is to provide a novel compound which solves the defects of conventional base precursors.

More specifically, a primary object of this invention is to provide a novel precursor which is extremely stable at normal temperature and smoothly decomposes under heating at 80° C. or higher to release a basic constituent.

Another object of the present invention is to provide a heat-developable photosensitive material which shows high S/N ratio and high image density.

The object of the present invention are achieved by a base precursor represented by the following general formula (I) or (II):

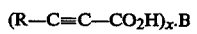   (I)

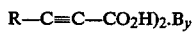   (II)

wherein, R represents a monovalent group selected from a hydrogen atom, an alkyl group, a substituted alkyl group, a cycloalkyl group, an alkenyl group, an alkynyl group, an aryl group, a substituted aryl group, a heterocyclic group, a substituted heterocyclic group, an aralkyl group, a substituted aralkyl group, an acyl group, an alkoxycarbonyl group, a carbamoyl group, a substituted carbamoyl group, —$CO_2M$ (M is an alkali metal), and —$CO_2H \cdot B$, or a divalent group selected from a unsubstituted and unsubstituted alkylene group, a substituted or unsubstituted arylene group and a substituted or unsubstituted heterocyclic divalent group.

B represents an organic base. x represents 1 and B is a monoacidic base, or 2 when B is a diacidic base. Y represents 2 when B is a monoacidic base, or 1 when B is a diacidic base.

DETAILED DESCRIPTION OF THE INVENTION

Examples of R include a hydrogen atom, an alkyl group of from 1 to 5 carbon atoms, a substituted alkyl group of from 1 to 5 carbon atoms, a cycloalkyl group of from 5 to 8 carbon atoms, an alkenyl group of from 2 to 5 carbon atoms, an alkynyl group of from 2 to 5 carbon atoms, a phenyl group, a substituted phenyl group, a naphthyl group, a substituted naphthyl group, an anthryl group, a pyridyl group, a substituted pyridyl group, a thienyl group, a substituted thienyl group, a thiazolyl group, a benzoxazolyl group, a benzthiazolyl group, a quinolyl group, a furanyl group, a pyrrolyl group, an imidazolyl group, a benzimidazolyl group, an aralkyl group of from 7 to 10 carbon atoms, a substituted aralkyl group such as a p-chlorobenzyl group, an acyl group of from 2 to 12 carbon atoms, an alkoxycarbonyl group of from 2 to 9 carbon atoms, a carbamoyl group, a substituted carbamoyl group of from 2 to 9 carbon atoms, —$CO_2Na$, —$CO_2K$, —$CO_2Cs$, —$CO_2H \cdot B$ (B is the afore-mentioned base constituent), a 1,3-phenylene group, a 1,4-phenylene group, a 1,5-naphthylene group, a 2,5-thienylene group, a 9,10-anthrylene group, and the like.

Examples of substituents on the group of R as described above include a halogen atom, an alkyl group, an alkoxy group, an aryl group, an acyl group, an acylamino group, an alkoxycarbonyl group, a carbamoyl group, a dialkylcarbamoyl group, a sulfamoyl group, a dialkylsulfamoyl group, an alkylsulfonyl group, an arylsulfonyl group, a cyano group, a nitro group, a trifluoromethyl group and the like.

In order to possess a sufficient decomposition rate of base precursor, it is desirable that R has appropriate electron-withdrawability, and thus an alkenyl group, an alkynyl group, a phenyl group, a substituted phenyl group, a naphthyl group, a substituted naphthyl group, an anthryl group, a pyridyl group, a substituted pyridyl group, a thienyl group, a substituted thienyl group, a benzoxazolyl group, a benzthiazolyl group, an acyl group, an alkoxycarbonyl group, a carbamoyl group, a substituted carbamoyl group, —$CO_2M$, —$CO_2H \cdot B$, a phenylene group, a naphthylene group, a thienylene group, an anthrylene group, etc. are preferably used. With respect to availability of raw materials, ease of preparation, etc., compounds represented by the following general formula (III) or (IV) are more preferably used:

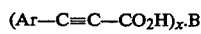   (III)

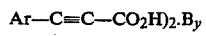   (IV)

wherein, Ar represents a phenyl group, a substituted phenyl group, a naphthyl group, a substituted naphthyl group, an anthryl group, a pyridyl group, a substituted pyridyl group, a thienyl group, a substituted thienyl group or divalent residual groups derived from these groups, and B, x and y have the same meaning as described above.

Base part B represents an organic base, and is preferably one having a pKa of not less than 9 and a boiling point of not less than 100° C. An organic base having a pKa of not less than 10, substantially no volatility at normal temperature (20° to 40° C.) and no bad odor is most preferred. Examples of organic base include guanidines, cyclic guanidine, amidines, cyclic amidines, etc. Furthermore, it is desirable that the base part B has hydrophilicity, and that it has a total carbon number of not more than 10. The following are preferred examples of base part B.

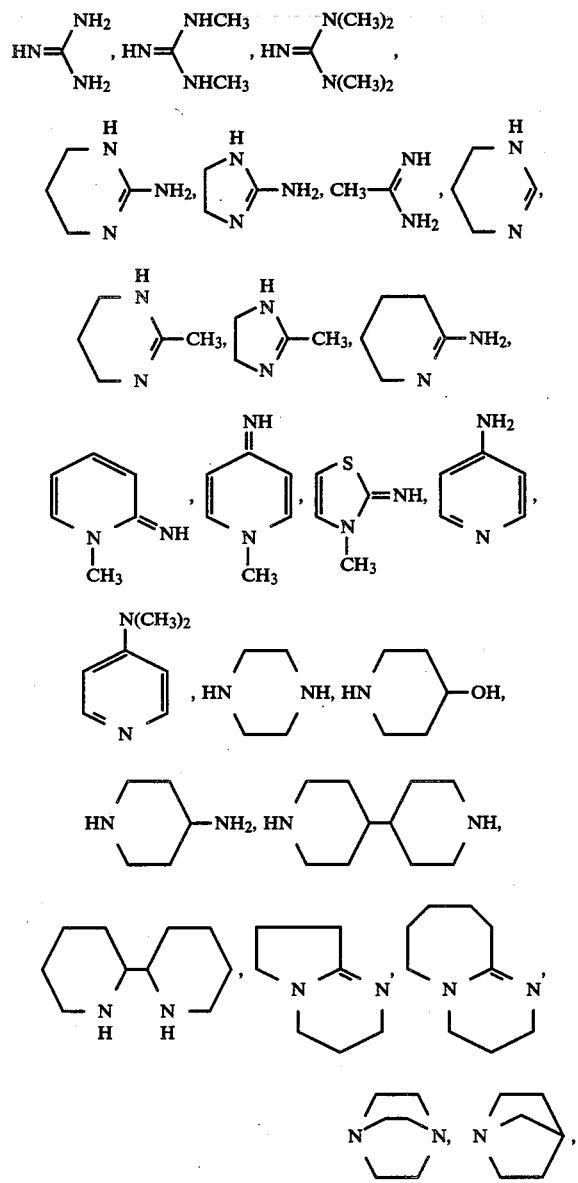

Structural characteristic of the base precursor of this invention are such that the acid part is a propiolic acid derivative and thus possesses a triple bond at the α-position of the carboxyl group, which causes considerably easy decarboxylation of the carboxylic acid. However, propiolic acid derivatives are extremely stable at normal temperature (20° to 40° C.), and the base constituent is released only by heating. As a result, it becomes possible to reconcile the stability during preservation at normal temperature and rapid decomposition (base release) during developing process (at a temperature of 80° C. or higher, preferably 100° C. or higher), which are required of the base precursor.

Thus, it becomes possible to provide an excellent heat-developable photosensitive material which improves the precedent defects by employing the base precursor of the present invention.

The followings are specific examples of base precursor of the present invention, but the present invention is in no way limited to these compounds:

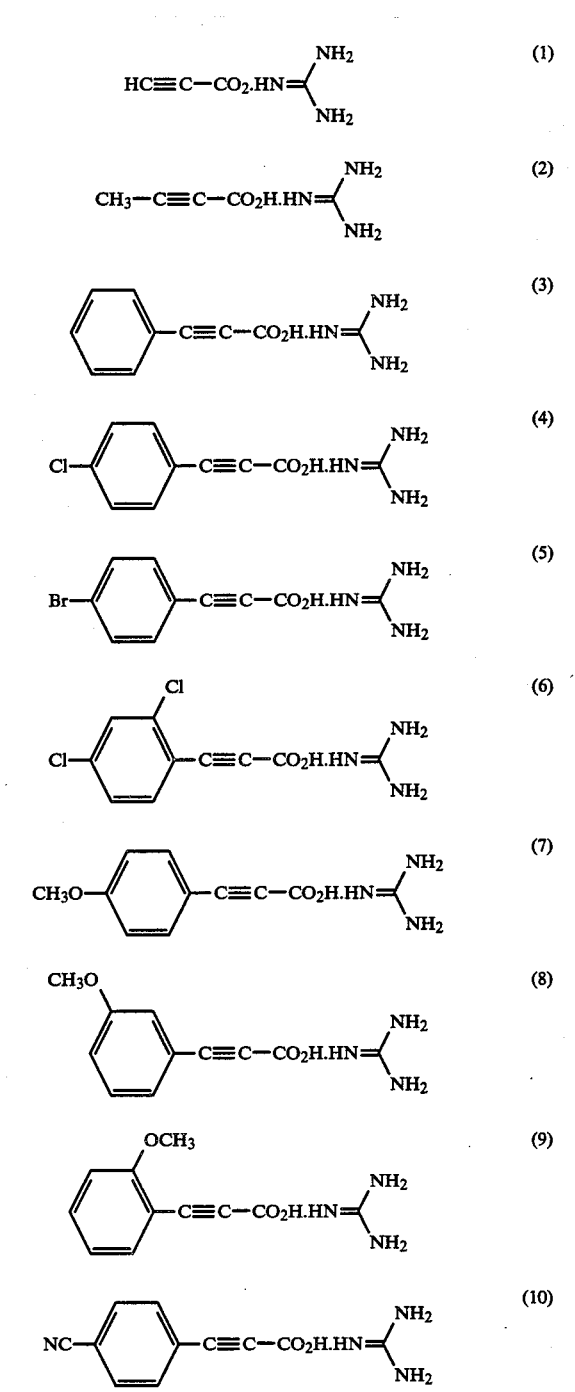

-continued
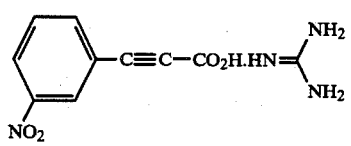 (11)
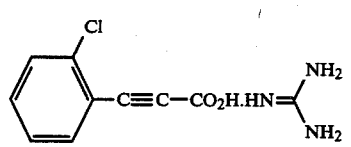 (12)
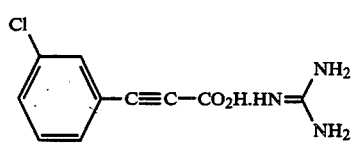 (13)
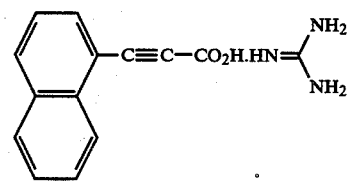 (14)
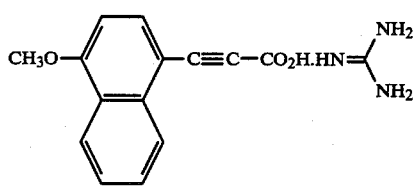 (15)
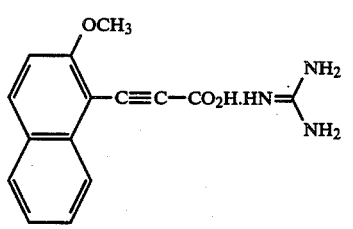 (16)
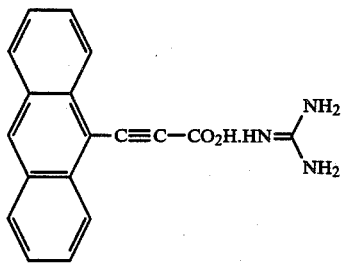 (17)
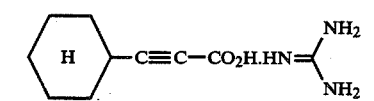 (18)
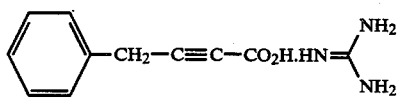 (19)
-continued
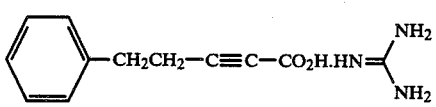 (20)
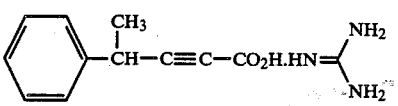 (21)
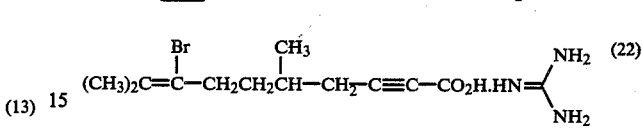 (22)
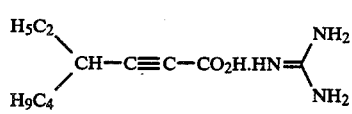 (23)
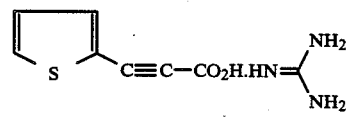 (24)
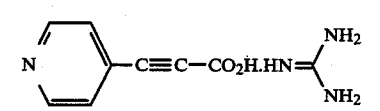 (25)
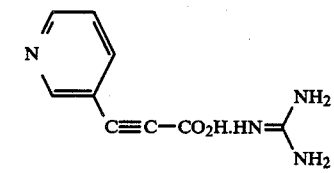 (26)
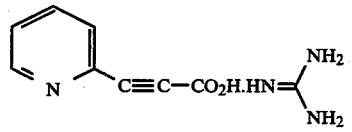 (27)
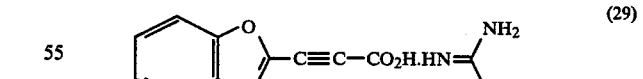
 (28)
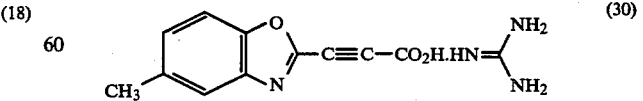 (29)
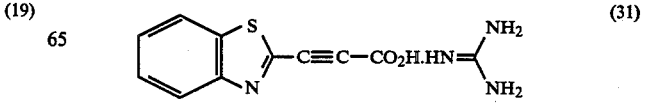 (30)
(31)

-continued
(32) 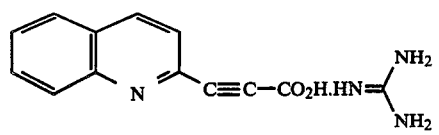
(33) 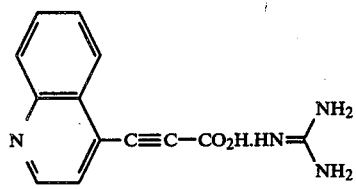
(34) 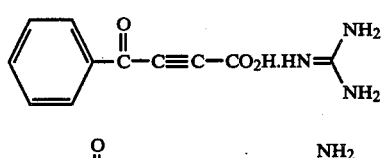
(35) 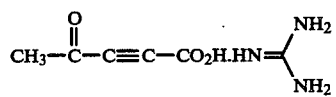
(36) 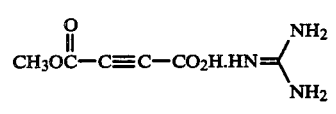
(37) 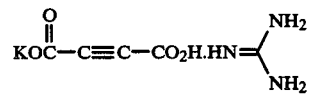
(38) 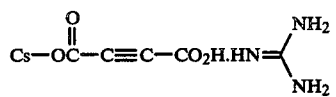
(39) 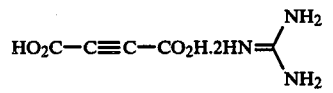
(40) 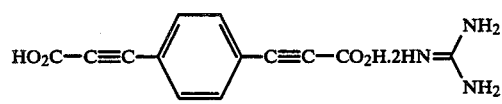
(41) 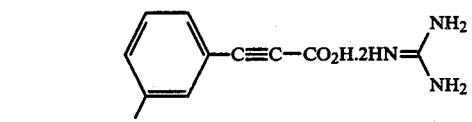
(42) 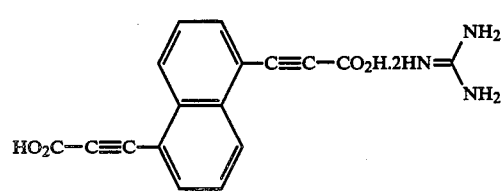
(43) 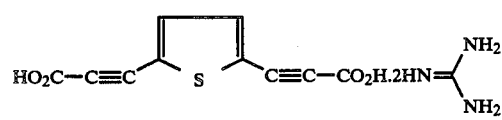
-continued
(44) 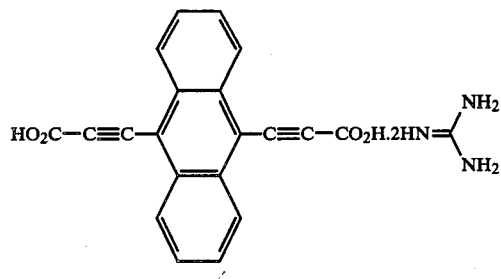
(45) 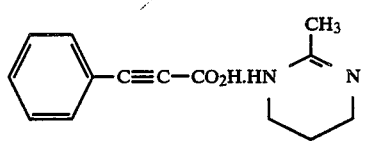
(46) 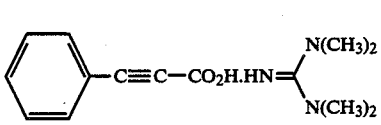
(47) 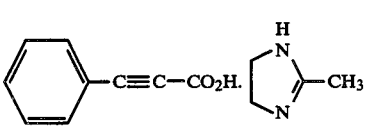
(48) 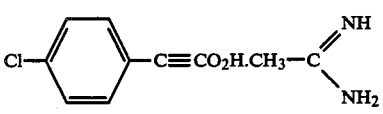
(49) 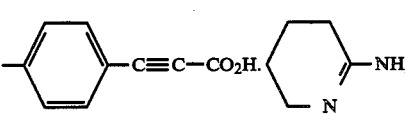
(50) 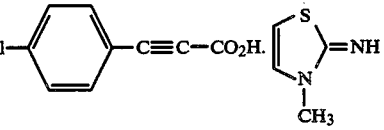
(51) 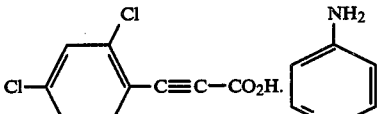
(52) 
(53) 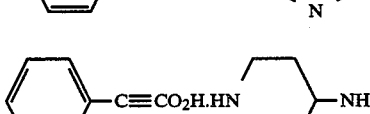
(54) 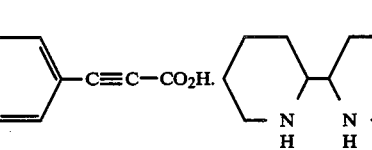

Methods of preparing the base precursors of the present invention are described below The base precursors of the present invention can be generally prepared by the following reaction scheme.

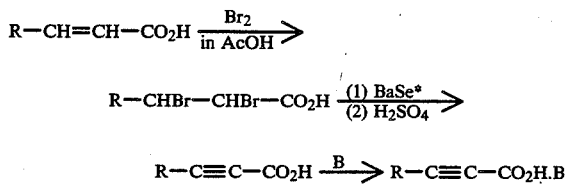

*KOH/CH₃OH, Diazobicycloundecane, etc.

According to this reaction scheme, propiolic acid derivatives are obtained by dehydrobromination with a strong base, after incorporation of bromine to acrylic acid derivatives.

SYNTHESIS EXAMPLE 1

Preparation of base precursor (3)

Cinnamic acid (29.6 g) was dissolved in acetic acid (80 ml) under heating and then bromine (32 g) was added dropwise. After stirring at 50° C. for 15 minutes, the resulting mixture was allowed to cool under standing and water (100 ml) was gradually added. The white crystals formed were filtered, washed with water and dried (yield: 56 g). Potassium hydroxide (56 g) was dissolved into methanol (20 ml) and then the above crystals were added in small portions to this solution. The methanol was removed under stirring with heating over a water bath. The residue was dissolved into 200 ml of water and neutralized with a diluted sulfuric acid under ice cooling. Freed pale yellow oil rapidly solidified. The solidified crystals were filtered and recrystallized from water to afford phenylpropiolic acid (22 g).

A mixture of phenylpropiolic acid (14.6 g), guanidine carbonate (9.0 g) and methanol (50 ml) was stirred at room temperature for 2 hours. Removal of the methanol under reduced pressure (not more than 50° C). afforded base precursor (3) as white crystals (20.2 g) having a melting point (decomposition point) of 137° to 139° C.

SYNTHESIS EXAMPLE 2

Preparation of base precursor (4)

After a mixture of p-chlorocinnamic acid (36.5 g) and acetic acid (100 ml) was heated at 50° C., bromine (35 g) was added dropwise. After stirring at 50° C. for 1 hour, the resulting mixture was allowed to cool and ice water (100 ml) was added. The white crystals formed were filtered, washed with water and dried (yield: 58 g).

The crystals (34.3 g) were gradually added to methanol (200 ml) containing sodium hydroxide (42 g) and the methanol was evaporated to dryness by stirring with heating over a water bath. The resulting residue was recrystallized from water to afford potassium p-chlorophenylpropionate as white crystals. These crystals were dissolved into 100 ml of water and neutralized with a diluted sulfuric acid to afford white crystals, which give 14.1 g of p-chlorophenylpropiolic acid after filtration, washing with water and drying.

After stirring of a mixture of p-chlorophenylpropiolic acid (10.8 g), guanidine carbonate (5.4 g) and methanol (50 ml) for 1 hour the methanol was removed under reduced pressure to afford 14 g of base precursor (4) as white crystals having a melting point (decomposition point) of 186° to 187° C.

SYNTHESIS EXAMPLE 3

Preparation of base precursor (6)

Bromine (32 g) was added dropwise into a mixture of 2,4-dichlorocinnamic acid (43.4 g) and acetic acid (200 ml) at 50° C., and the whole was stirred at 60° to 70° C. for 2 hours. After cooling, ice-water (200 ml) was added and white precipitates formed were filtered, washed with water and dried (yield: 57.7 g). The resulting dibromide was added to a mixture of potassium hydroxide (56 g) and methanol (200 ml) at room temperature, and then the methanol was removed by heating with stirring over a water bath. A mixture of potassium hydroxide (28 g) and methanol (200 ml) was added to the residue, and a similar procedure was carried out. The residue was recrystallized from 1.5 l of hot water to afford potassium 2,4-dichlorophenylpropiolate as white crystals. This potassium salt was suspended in hot water and neutralized by a diluted hydrochloric acid to afford 2,4-dichlorophenylpropiolic acid (22.8 g) having a melting point of 161° to 163° C.

A solution of 2,4-dichlorophenylpropiolic acid (17.2 g) dissolved in methanol (80 ml) was added to a solution of guanidine carbonate (7.2 g) dissolved in water (40 ml). After stirring at room temperature for 30 minutes, the methanol was removed under reduced pressure, and then white crystals were filtered and washed with water to afford 16.4 g of base precursor (6) having a melting point of 177° to 179° C.

SYNTHESIS EXAMPLE 4

Preparation of base precursor (37)

To a mixture of potassium hydroxide (44.8 g) and methanol (200 ml) was added 2,3-dibromosuccinic acid (55.2 g), and the whole was heated under reflux for 5 hours over a water bath. After cooling, white crystals were filtered and washed with methanol to afford a mixture (89 g) of acetylenedicarboxylic acid di-potassium salt and potassium bromide. The mixture was dissolved in water (as little water as possible was used) and 6N sulfuric acid (36 ml) was carefully added. White crystals formed were filtered to give 12.8 g of acetylenedicarboxylic acid mono-potassium salt.

The above mono-potassium salt (7.7 g) was dissolved in water (30 ml) and then guanidine carbonate (4.5 g) was added portionwise. After stirring at room temperature for 30 minutes, the water was removed under reduced pressure and methanol was added to the residue. White crystals were filtered to afford 8.2 g of base precursor (37) having a melting point of 171° to 173° C.

Base precursor of the present invention can be used in various heat-developable image forming methods.

For example, the base precursor may be used in the heat-developable diazo copying material(s), which is described in Japanese Patent Application (OPI) Nos. 11229/75, 109924/77, 45094/82, 133033/80 and 150014/77, and Japanese Patent Publication Nos. 19620/81, 24726/68, 40455/76, 41202/73 and 28663/69.

In a method using heat-developable diazo copying material, the photosensitive layer contains a photosensitive diazo compound, a coupling constituent and a compound which releases a base by heating, i.e., a base precursor. By heating the material to 100° to 200° C., an azo dye was formed by a coupling reaction.

A compound of the present invention can be applied to the above-mentioned heat-developable diazo copying material and analogous methods.

Heat-developable photosensitive materials using silver halide were described in, for example, Shashin Kogaku no Kiso, pp. 553-555, published by Corona Co. (1977), Eizo Jōhō, p. 40, April, 1978, *Nebletts Handbook of Photography and Reprography*, 7th, Ed., pp. 32-33, published by Van Nostrand Reinhold Company, U.S. Pat. Nos. 3,152,904, 3,301,678, 3,392,020, 3,457,075, 3,531,286, 3,761,270, 3,985,565, 4,021,240, 4,022,617, 4,235,957, British Pat. Nos. 1,131,108, 1,167,777, Belgian Patent No. 802,519, and Research Disclosure, pp. 54-58, May 1978 (RD-16966), ibid., pp. 9-15, June 1978 (RD-17029), ibid. pp. 30-32, April 1976 (RD-14453), ibid., pp. 14-15, December 1976 (RD-15227), etc.

When carrying out the heat-developing methods using silver halide, photosensitive materials having on a support layers containing (1) photosensitive silver halide emulsion, (2) a composition which release base by heating and (3) a developing agent for silver halide were used. After image exposure of these photosensitive materials, the developing agent becomes active to developing by the action of the base with heating, and then, silver halides exposed were reduced to afford silver images.

Compounds of the present invention can be applied to the above-mentioned heat-developable photosensitive materials using silver halide and analogous methods.

Moreover, these can be employed in heat-sensitive materials described in Japanese Patent Publication No. 29024/76, and Japanese Patent Application (OPI) Nos. 147949/75, 82421/78 and 99951/78.

Base precursors of the present invention can release base efficiently in the state existing substantially in dry film. Therefore, it is advantageous to use the base precursor of the present invention when it is intended to cause some chemical change by the action of the base released by heating.

The amount of base precursor to be used depends on the compound and the system used. In general, an amount of 0.01 to 50 wt% calculated based on the weight of the coated film is used and a range of not more than 30 wt% is preferred. Base precursors of the present invention can be used alone or in combination. Furthermore, they can be used together with base precursor(s) other than those of the present invention.

Base precursors of the present invention can be contained in a binder by dissolving it in a water-soluble organic solvent (e.g., methanol, ethanol, acetone and dimethylformamide) or a mixture of these organic solvents and water.

The present invention will be specifically described by the following Examples. However, the scope of the present invention is in no way limited to these Examples.

EXAMPLE 1

Application to heat-developable silver halide photosensitive material:

A photosensitive material was prepared by applying the following composition homogeneously to form a thickness of 60 μm and drying.

| | |
|---|---|
| (a) silver iodobromide emulsion (containing 10 mol % of silver iodide and 5 wt % of gelatin and silver) | 10 g |
| (b) gelatin (10% aqueous solution) | 5 g |
| (c) a solution of 0.2 g of 2,6-dichloro-p-aminophenol dissolved in 15 cc of water | |
| (d) coupler dispersion prepared as described below | 3.5 g |

-continued

| | |
|---|---|
| (e) a solution of 0.25 g of base precursor (3) of the present invention dissolved in 2.5 cc of methanol | |

The coupler dispersion was prepared by the following method.

Tri-cresyl phosphate (TCP) (2.5 g), 2-dodecylcarbamoyl-1-naphthol (5 g) and succinic acid-2-ethyl-hexyl ester sodium sulfonate (0.5 g) were weighed and dissolved in ethyl acetate (30 ml). This solution was mixed with a 10% gelatin solution (100 g) and dispersed by stirring.

The photosensitive material thus prepared was image exposed at 2000 luxes for 5 seconds using a tangusten bulb. Then, the material was heated homogeneously for 20 seconds over a heat block heated at 140° C. to afford negative cyan color image. The density of this image was measured by means of a Macbeth (phonetic) transmittance densitometer (TD-504). As a result of the measurement, it was found that the maximum density was 2.15 and the minimum density was 0.18.

Next, in order to test the preservability of this photosensitive material, the photosensitive material was stored at 50° C. for 2 days, then exposed and thermally developed under similar conditions as described above. The results showed a maximum density of 2.30 and a minimum density of 0.30.

COMPARATIVE EXAMPLE

A photosensitive material was prepared in the same manner as in Example 1 using a conventional base precursor, trichloroacetic acid guanidine (0.28 g) instead of base precursor (3) of the present invention, and tested. As a result, the following values are obtained.

| | Maximum Density | Minimum Density |
|---|---|---|
| Fresh | 2.13 | 0.28 |
| After stored at 50° C. for 2 days | 2.18 | 1.65 |

The above results clearly show that the base precursor of the present invention is stable during preservation and has high activity during the developing process.

EXAMPLE 2

A photosensitive material was prepared in a manner similar to Example 1 using the following base precursors instead of base precursor (3) of the present invention. The material prepared was tested and the following results were obtained, which show that all the base precursors of the present invention are favorable.

| Base Precursor No. | Amount Added (g) | Maximum Density | Minimum Density |
|---|---|---|---|
| (4) | 0.28 | 2.25 | 0.20 |
| (8) | 0.28 | 2.12 | 0.18 |
| (14) | 0.35 | 2.16 | 0.18 |
| (24) | 0.28 | 2.18 | 0.22 |
| (27) | 0.25 | 2.21 | 0.21 |
| (40) | 0.25 | 2.05 | 0.21 |
| (45) | 0.30 | 2.10 | 0.35 |
| (46) | 0.28 | 2.28 | 0.32 |

EXAMPLE 3

Application to heat-developable diazo copying material

On a polyethylene terephthalate support, a heat-developable diazo composition was applied so as to form a thickness of 100 μm when wet. The composition used included a mixture of the following constituents.

| | | |
|---|---|---|
| (a) | [naphthoquinone diazide with SO₂Cl structure] | 30 mg |
| (b) | [benzothiazolium compound with C₂H₅SO₄⁻ counterion] | 60 mg |
| (c) | base precursor (3) of the present invention | 100 mg |
| (d) | 10% methylene chloride solution of polyvinylidene chloride | 5 ml |
| (e) | acetone | 5 ml |

After drying, the resulting material was irradiated by ultraviolet light for 1 minute through transparent text original by means of a usual diazo exposing apparatus, and thermally developed homogeneously for 30 seconds on a heat block heated at 140° C. Reddish brown colored positive image having optical density of 1.15 was obtained.

While the invention has been described in detail and with reference to specific embodiment thereof, it will be apparent to one skilled in the art that various changes and modifications can be made therein without departing from the spirit and scope thereof.

What is claimed is:

1. A base precursor for heat-developable photosensitive material, represented by the general formula (I) or (II):

$$(R-C\equiv C-CO_2H)_x \cdot B \quad (I)$$

$$R-C\equiv C-CO_2H)_2 \cdot B_y \quad (II)$$

wherein, R represents a monovalent group selected from the group consisting of a hydrogen atom, an alkyl group, a substituted alkyl group, a cycloalkyl group, an alkenyl group, an alkynyl group, an aryl group, a substituted aryl group, a heterocyclic group, a substituted heterocyclic group, an aralkyl group, a substituted aralkyl group, an acyl group, an alkoxycarbonyl group, a carbamoyl group, a substituted carbamoyl group, $-CO_2M$ (M is an alkali metal) and $-CO_2H \cdot B$, or a divalent group selected from the group consisting of a substituted or unsubstituted alkylene group, a substituted or unsubstituted arylene group and a substituted or unsubstituted heterocyclic divalent group;

B represents an organic base;

x represents 1 when B is a monoacidic base, and 2 when B is a diacidic base; and y represents 2 when B is a monoacidic base, and 1 when B is a diacidic base.

2. A base precursor as claimed in claim 1, wherein R is selected from the group consisting of a hydrogen atom, an alkyl group containing 1 to 5 carbon atoms, a substituted alkyl group containing 1 to 5 carbon atoms, a cycloalkyl group containing 5 to 8 carbon atoms, an alkenyl group containing 2 to 5 carbon atoms, an alkynyl group containing 2 to 5 carbon atoms, a phenyl group, a substituted phenyl group, a naphthyl group, a substituted naphthyl group, an anthryl group, a pyridyl group, a substituted pyridyl group, a thienyl group, a substituted thienyl group, a thiazolyl group, a benzoxazolyl group, a benzthiazolyl group, a quinolyl group, furanyl group, a pyrrolyl group, an imidazolyl group, a benzimidazolyl group, an aralkyl group containing 7 to 10 carbon atoms, a p-chlorobenzyl group, an acyl group containing 2 to 12 carbon atoms, an alkoxycarbonyl group containing 2 to 9 carbon atoms, a carbamoyl group, a substituted carbamoyl group containing 2 to 9 carbon atoms, $-CO_2Na$, $-CO_2K$, $-CO_2Cs$, $-CO_2H \cdot B$, a 1,3-phenylene group, a 1,4-phenylene group, a 1,5-naphthylene group, a 2,5-thienylene group, and a 9,10-anthrylene group.

3. A base precursor as claimed in claim 1, wherein the compound represented by the general formula (I) or (II) is a compound represented by the general formula (III) or (IV):

$$(Ar-C\equiv C-CO_2H)_x \cdot B$$

$$Ar-C\equiv C-CO_2H)_2 \cdot B_y$$

wherein Ar is selected from the group consisting of a phenyl group, a substituted phenyl group, a naphthyl group, a substituted naphthyl group, an anthryl group, a pyridyl group, a substituted pyridyl group, a thienyl group, a substituted thienyl group and divalent groups derived from these groups.

4. A base precursor as claimed in claim 3, wherein B is an organic base having a pKa of not less than 9 and a boiling point of not less than 100° C.

5. A base precursor as claimed in claim 4, wherein B is an organic base having a pKa of not less than 10 and substantially no volatility at a temperature in the range of 20° C. to 40° C.

* * * * *